United States Patent [19]

Nagano et al.

[11] Patent Number: 4,709,049

[45] Date of Patent: * Nov. 24, 1987

[54] 2-SUBSTITUTED PHENYL-4,5,6,7,-TETRAHYDRO-2H-INDOLE-1,3,-DIONES, AND THEIR PRODUCTION AND USE

[75] Inventors: Eiki Nagano, Nishinomiya; Ryo Yoshida, Kawanishi; Hiroshi Matsumoto, Kakogawa; Shunichi Hashimoto, Kobe; Katsuzo Kamoshita, Osaka, all of Japan

[73] Assignee: Sumitomo Chemical Company, Limited, Osaka, Japan

[*] Notice: The portion of the term of this patent subsequent to Aug. 4, 2004 has been disclaimed.

[21] Appl. No.: 744,943

[22] Filed: Jun. 17, 1985

Related U.S. Application Data

[63] Continuation-in-part of Ser. No. 609,019, May 10, 1984, abandoned.

[30] Foreign Application Priority Data

May 16, 1983 [JP] Japan ................................. 58-86213

[51] Int. Cl.$^4$ ............................................ C07D 209/48
[52] U.S. Cl. .................................... 548/513; 71/96; 260/507 R; 260/543 R; 562/431; 564/218
[58] Field of Search ............................. 548/513; 71/96

[56] References Cited

U.S. PATENT DOCUMENTS

| | | | |
|---|---|---|---|
| 3,235,605 | 2/1966 | Napolitano | 568/69 |
| 3,465,001 | 9/1969 | Bolhofer et al. | 548/513 |
| 3,878,224 | 4/1975 | Matsui et al. | 71/94 |
| 3,954,442 | 5/1976 | Becker et al. | 71/108 |
| 3,984,435 | 10/1976 | Matsui et al. | 71/96 |
| 4,001,272 | 1/1977 | Goddard | 71/96 |
| 4,032,326 | 6/1977 | Goddard | 71/96 |
| 4,124,375 | 11/1978 | Bollinger et al. | 71/96 |
| 4,157,256 | 6/1979 | Hiraga et al. | 71/95 |
| 4,292,070 | 9/1981 | Wakabayashi et al. | 71/96 |
| 4,349,377 | 9/1982 | Durr et al. | 71/98 |
| 4,420,327 | 12/1983 | Jikihara et al. | 548/513 |
| 4,431,822 | 2/1984 | Nagano et al. | 548/513 |
| 4,439,229 | 3/1984 | Swithenbank | 71/96 |
| 4,484,940 | 11/1984 | Nagano et al. | 71/96 |
| 4,484,941 | 11/1984 | Nagano et al. | 71/96 |
| 4,536,209 | 8/1985 | Jikihara et al. | 71/96 |

FOREIGN PATENT DOCUMENTS 0049508A 4/1982 European Pat. Off. .
0061741A 10/1982 European Pat. Off. .

(List continued on next page.)

OTHER PUBLICATIONS

G. Pagani et al, Farmaco, Ed. Sci., 33(5), 332–349, (1978).

(List continued on next page.)

Primary Examiner—Mary E. Ceperley
Attorney, Agent, or Firm—Birch, Stewart, Kolasch & Birch

[57] ABSTRACT

3-Amino-4-fluoro-6-halophenylthioacetic acids of the formula:

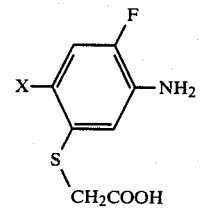

and 5-substituted acetanilides of the formula:

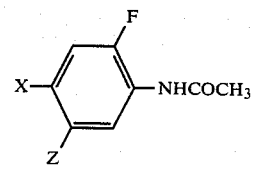

, which are intermediary compounds for the synthesis of herbicidally effective 2-substituted phenyl-4,5,6,7-tetrahydro-2H-isoindole-1,3-diones of the formula:

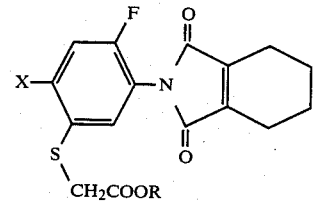

through the corresponding acid of the formula:

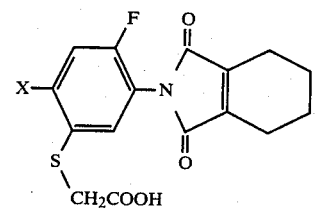

(wherein X is a chlorine atom or a bromine atom, R is a $C_1$–$C_6$ alkyl group, a $C_3$–$C_7$ cycloalkyl group, a $C_3$–$C_6$ alkenyl group, a $C_3$–$C_6$ alkynyl group, a $C_2$–$C_6$ haloalkyl group, a $C_1$–$C_4$ alkoxy($C_1$–$C_4$)alkyl group, a $C_1$–$C_6$ alkoxycarbonyl($C_1$–$C_3$)alkyl group or a phenyl group and Z is —$NO_2$, —$NH_2$, —$SCH_2COOH$, —$SO_2Cl$, —$SO_3H$ or —SH).

3 Claims, No Drawings

FOREIGN PATENT DOCUMENTS

| | | | |
|---|---|---|---|
| 0067352 | 12/1982 | European Pat. Off. | 562/431 |
| 0067354 | 12/1982 | European Pat. Off. | |
| 0068822A | 1/1983 | European Pat. Off. | |
| 0077938A | 5/1983 | European Pat. Off. | |
| 83055A | 7/1983 | European Pat. Off. | 71/96 |
| 0126419 | 11/1984 | European Pat. Off. | |
| 2433013A | 3/1980 | France. | |
| 55-130954 | 10/1980 | Japan. | |
| 57-24355 | 8/1982 | Japan. | |
| 2005668A | 4/1979 | United Kingdom. | |
| 2046754A | 11/1980 | United Kingdom. | |
| 213814 | 3/1968 | U.S.S.R.. | |

OTHER PUBLICATIONS

G. Pagani et al., Chem. Abst., 89:42719j, (1978).
C. Swithenbank, Chem. Abst., 98:215478w, (1983).
R. Giraudon, Chem. Abst., 93:114150z, (1980).
R. Morrison et al., Organic Chemistry, 2nd Ed., p. 602.
Chemical Abstracts, 101, 146132v, (1984).
Chemical Abstracts, 101, 124918d, (1984).
Chemical Abstracts, 101, 124919e, (1984).
G. C. Finger, Plant Growth Regulators and Intermediates.
PCT Publication WO80/00341, Mar. 3, 1982.

2-SUBSTITUTED PHENYL-4,5,6,7,-TETRAHYDRO-2H-INDOLE-1,3,-DIONES, AND THEIR PRODUCTION AND USE

This is a continuation-in-part application of our copending application Ser. No. 609,019 filed on May 10, 1984, now abaonded.

The present invention relates to 2-substituted phenyl-4,5,6,7-tetrahydro-2H-isoindole-1,3-diones (hereinafter referred to as "isoindole(s)"), and their production and use.

The said isoindoles are representable by the formula:

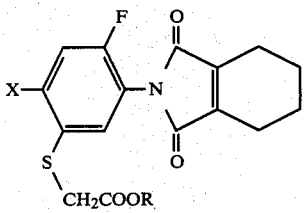

wherein X is a chlorine atom or a bromine atom and R is a $C_1$–$C_6$ alkyl group, a $C_3$–$C_7$ cycloalkyl group, a $C_3$–$C_6$ alkenyl group, a $C_3$–$C_6$ alkynyl group, a $C_2$–$C_6$ haloalkyl group, a $C_1$–$C_4$ alkoxy($C_1$–$C_4$)alkyl group, a $C_1$–$C_6$ alkoxycarbonyl($C_1$–$C_3$)alkyl group or a phenyl group.

It is known that certain kinds of isoindoles are effective as herbicides. For instance, the herbicidal use of 2-(4-chlorophenyl)-4,5,6,7-tetrahydro-2H-isoindole-1,3-dione is disclosed in U.S. Pat. Nos. 3,878,224 and 3,984,435. However, their herbicidal effect is not necessarily satisfactory.

It has now been found that the isoindoles (I) show a strong herbicidal activity against a wide variety of weeds including broad-leaved weeds, Graminaceous weeds and Cyperaceous weeds in upland field as well as weeds in paddy field at small doses and do not produce any material phytotoxicity on various agricultural crops such as corn, soybean, wheat, peanut and rice plant. Examples of broadleaved weeds are wild buckwheat (*Polygonum convolvulus*), pale smartweed (*Polygonum lapathifolium*), common purslane (*Portulaca oleracea*), common lambsquarters (*Chenopodium album*), redroot pigweed (*Amaranthus retroflexus*), radish (*Raphanus sativus*), hemp sesbania (*Sesbania exaltata*), velvetleaf (*Abutilon theophrasti*), prickly sida (*Sida spinosa*), field pansy (*Viola arvensis*), wild carrot (*Daucus carota*), catchweed bedstraw (*Galium aparine*), ivyleaf morningglory (*pomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), Persian speedwell (*Veronica persica*), ivyleaf speedwell (*Veronica hederaefolia*), cocklebur (*Xanthium strumarium*), sunflower (*Helianthus annuus*), scentless chamomile (*Matricaria perforata*), false pimpernel (*Lindernia procumbens*), Indian toothcup (*Rotala indica*), waterwort (*Elatine triandra*), etc. Examples of Graminaceous weeds against which the isoindoles (I) show a herbicidal activity are Japanese millet (*Echinochloa frumentacea*), barnyardgrass (*Echinochloa crus-galli*, *Echinochloa oryzicola*), green foxtail (*Setaria viridis*), large crabgrass (*Digitaria sanguinalis*), etc. Examples of Cyperaceous weeds are rice flatsedge (*Cyperus iria*), etc. Accordingly, the isoindoles (I) can be used as herbicides applicable to upland field as well as paddy field.

The herbicidal activity of the isoindoles (I) is particularly notable on post-emergence foliar treatment of broad-leaved weeds such as cocklebur, tall monrningglory, velvetleaf, redroot pigweed, black nightshade, hemp sesbania, common lambsquarters, prickly sida and field bindweed, especially velvetleaf, redroot pigweed and black nightshade, in a soybean, corn or peanut field, especially in a soybean field, because the isoindoles (I) do not afford any material phytotoxicy to soybean, corn or peanut, particularly to soybean.

Among the isoindoles (I), preferable are those of the formula (I) wherein R is a $C_1$–$C_6$ alkyl group, a $C_5$–$C_6$ cycloalkyl group, a $C_3$–$C_6$ alkenyl group, a $C_3$–$C_6$ alkynyl group, a $C_2$–$C_6$ haloalkyl group or a methoxy($C_1$–$C_4$)alkyl group. More preferable are those of the formula (I) wherein X is a chlorine atom and R is a $C_1$–$C_6$ alkyl group, a $C_5$–$C_6$ cycloalkyl group, an allyl group or a propargyl group. Most preferable is 2-(4-chloro-2-fluoro-5-cyclopentyloxycarbonylmethylthiophenyl)-4,5,6,7-tetrahydro-2H-isoindole -1,3-dione.

The isoindole (I), which is novel, is obtainable by reacting an N-(m-carboxymethylthiophenyl)tetrahydrophthalimide of the formula:

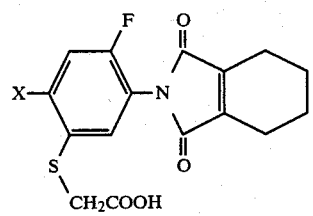

wherein X is as defined above with an alcohol of the formula:

R—OH (III)

wherein R is as defined above.

The reaction is usually carried out in a solvent in the presence of a dehydrating agent, if necessary, with a base, at a temperature of from 0° to 200° C. for a period of 1 to 24 hours. When desired, the reaction may be carried out while removal of water from the reaction system. The alcohol (III) is normally employed in an amount of 1.0 to 10 equivalents to the starting compound (II). The amount of the dehydrating agent may be ordinarily from a catalytic amount to 1 equivalent to the starting compound (II). Examples of the solvent are aliphatic hydrocarbons (e.g. hexane, heptane, ligroin, petroleum ether), aromatic hydrocarbons (e.g. benzene, toluene, xylene,), halogenated hydrocarbons (e.g. chloroform, carbon tetrachloride, methylene chloride), ethers (e.g. diethyl ether, diisopropyl ether, dioxane, tetrahydrofuran, diethylene glycol dimethyl ether), etc. Examples of the dehydrating agent are an acid (e.g. conc. sulfuric acid, p-toluenesulfonic acid), a carbodiimides (e.g. dicyclohexylcarbodiimide), etc. As the base, there may be exemplified an aminopyridine (e.g. 4-N,N-dimethylaminopyridine).

The reaction mixture is usually subjected to ordinary post-treatment such as extraction with an organic solvent and concentration to recover the produced isoindole (I). When desired, the product may be purified by a per se conventional procedure such as column chromatography or recrystallization.

Practical and presently preferred embodiment for the production of the isoindoles (I) is as follows:

Example 1

To a solution of 2-(4-chloro-2-fluoro-5-carboxymethylthiophenyl)-4,5,6,7-tetrahydro-2H-isoindole-1,3-dione (1.2 g) and ethanol (1.0 g) in toluene (20 ml), there was added a small amount of p-toluenesulfonic acid, and the mixture was refluxed for 3 hours. Water was added to the reaction mixture. The toluene layer was separated, dried and concentrated. The residue was purified by silica gel chromatography to give 0.1 g of 2-(4-chloro-2-fluoro-5-ethoxycarbonylmethylthiophenyl-4,5,6,7-tetrahydro-2H-isoindole-1,3-dione. $n_D^{18}$ 1.5670.

NMR δ ppm (CDCl$_3$): 1.3 (3H, t), 3.6 (2H, s), 4.1 (2H, q), 7.2 (1H, d), 7.3 (1H, d).

IR ν cm$^{-1}$ (neat): 1720.

In the same manner as above, there were produced other isoindoles (I), of which typical examples are shown in Table 1.

TABLE 1

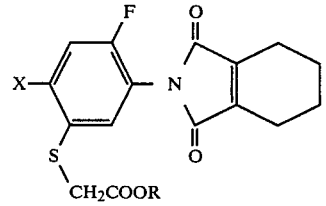

| Compound No. | X | R | Physical constant |
|---|---|---|---|
| 1 | Cl | —CH$_2$CH$_3$ | $n_D^{18}$ 1.5670 |
| 2 | Cl | —CH$_2$(CH$_2$)$_3$CH$_3$ | $n_D^{18.5}$ 1.5590 |
| 3 | Cl | —CH$_2$C≡CH | $n_D^{20}$ 1.5570 |
| 4 | Cl | —CH$_2$CH$_2$OCH$_3$ | $n_D^{18.5}$ 1.5695 |
| 5 | Cl | —CH$_2$CH$_2$Cl | $n_D^{21}$ 1.5740 |
| 6 | Cl | —CH$_2$—CH(Cl)—CH$_2$Cl | $n_D^{18.5}$ 1.5705 |
| 7 | Cl | cyclopentyl | $n_D^{18.5}$ 1.5640 |
| 8 | Cl | —CH$_2$CO$_2$CH$_2$CH$_3$ | $n_D^{18.5}$ 1.5420 |
| 9 | Br | —CH$_3$ | $n_D^{23.5}$ 1.5863 |
| 10 | Br | —CH$_2$CH$_2$Cl | Glassy |
| 11 | Br | cyclohexyl | Glassy |
| 12 | Br | phenyl | Glassy |
| 13 | Cl | —CH(CH$_3$)CH$_2$CH$_2$CH$_3$ | $n_D^{15.5}$ 1.5516 |
| 14 | Cl | —CH(CH$_2$CH$_3$)$_2$ | $n_D^{24}$ 1.5565 |

TABLE 1-continued

| Compound No. | X | R | Physical constant |
|---|---|---|---|
| 15 | Cl | —(CH$_2$)$_5$CH$_3$ | $n_D^{24.4}$ 1.5513 |
| 16 | Cl | —CH$_2$CH$_2$CH(CH$_3$)$_2$ | $n_D^{20.7}$ 1.5556 |
| 17 | Cl | —CH$_2$CH(CH$_3$)$_2$ | $n_D^{24.4}$ 1.5555 |
| 18 | Cl | —CH(CH$_3$)CH$_2$CH(CH$_3$)$_2$ | $n_D^{18.5}$ 1.5471 |
| 19 | Cl | —CH$_2$CH$_2$CH$_2$Cl | $n_D^{22.0}$ 1.5730 |
| 20 | Cl | —CH(CH$_2$Cl)$_2$ | $n_D^{23.7}$ 1.5650 |
| 21 | Cl | cyclohexyl | $n_D^{24.0}$ 1.5598 |
| 22 | Cl | —CH$_2$CH$_2$CH(OCH$_3$)CH$_3$ | $n_D^{18.5}$ 1.5538 |
| 23 | Cl | —CH$_2$CH$_2$C(OCH$_3$)(CH$_3$)$_2$ | $n_D^{18.5}$ 1.5652 |
| 24 | Cl | —CH(CH$_3$)CH$_2$OCH$_3$ | $n_D^{18.5}$ 1.5538 |
| 25 | Cl | —CH$_2$CH=CH$_2$ | $n_D^{21.3}$ 1.5750 |
| 26 | Cl | —CH$_2$CH=CHCH$_3$ | $n_D^{22.2}$ 1.5663 |
| 27 | Cl | —CH$_2$CH=C(CH$_3$)$_2$ | $n_D^{19.8}$ 1.5518 |
| 28 | Cl | —CH$_2$C(CH$_3$)=CH$_2$ | $n_D^{24.5}$ 1.5630 |

The starting N-(m-carboxymethylthiophenyl)tetrahydrophthalimide (II), which is novel, is obtainable by reacting an N-(m-aminophenyl)tetrahydrophthalimide of the formula:

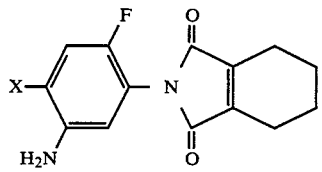

wherein X is as defined above with sodium nitrite in the presence of a mineral acid, normally in an inert solvent, at a temperature of −10° to 5° C. and reacting the resultant diazonium salt with thioglycollic acid in the existence of a divalent copper salt, usually in an inert solvent, at a temperature of 20° to 40° C.

The amounts of the sodium nitrite, the mineral acid, the thioglycollic acid and the divalent copper salt are respectively from 1.0 to 1.5 equivalents, from 1.0 to 10 equivalents, from 1.0 to 1.5 equivalents and from 0.5 to 1.2 equivalents to the compound (IV). As the mineral acid, there are exemplified hydrochloric acid, sulfuric acid, etc. Examples of the divalent copper salt are cupric sulfate, basic cupric carbonate, etc. Examples of the inert solvent are water, acetic acid, etc.

Said N-(m-aminophenyl)tetrahydrophthalimide (IV) is per se known and is obtainable, for example, by the method as described in EP0077938A.

The starting N-(m-carboxymethylthiophenyl)tetrahydrophthalimide (II) is also obtainable by reacting an aminophenylthioacetic acid of the formula:

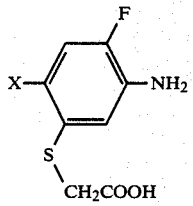

(V)

wherein X is as defined above with a 1.0 to 1.1 equivalent amount of 3,4,5,6-tetrahydrophtalic acid anhydride in an inert solvent at a temperature of 80 to 200° C. for a period of 0.5 to 12 hours. As the inert solvent, there may be employed water, acetic, acid, propionic acid, dioxane, etc. mixtures thereof are also usable.

The reaction mixture is usually subjected to ordinary post-treatment such as extraction with an organic solvent and concentration to recover the produced N-(m-carboxymethylthiophenyl)tetrahydrophthalimide (II). When desired, the product may be purified by a per se conventional procedure such as column chromatography or recrystallization.

The production of said aminophenylthioacetic acid (V), which is novel, may be summarized in the following scheme:

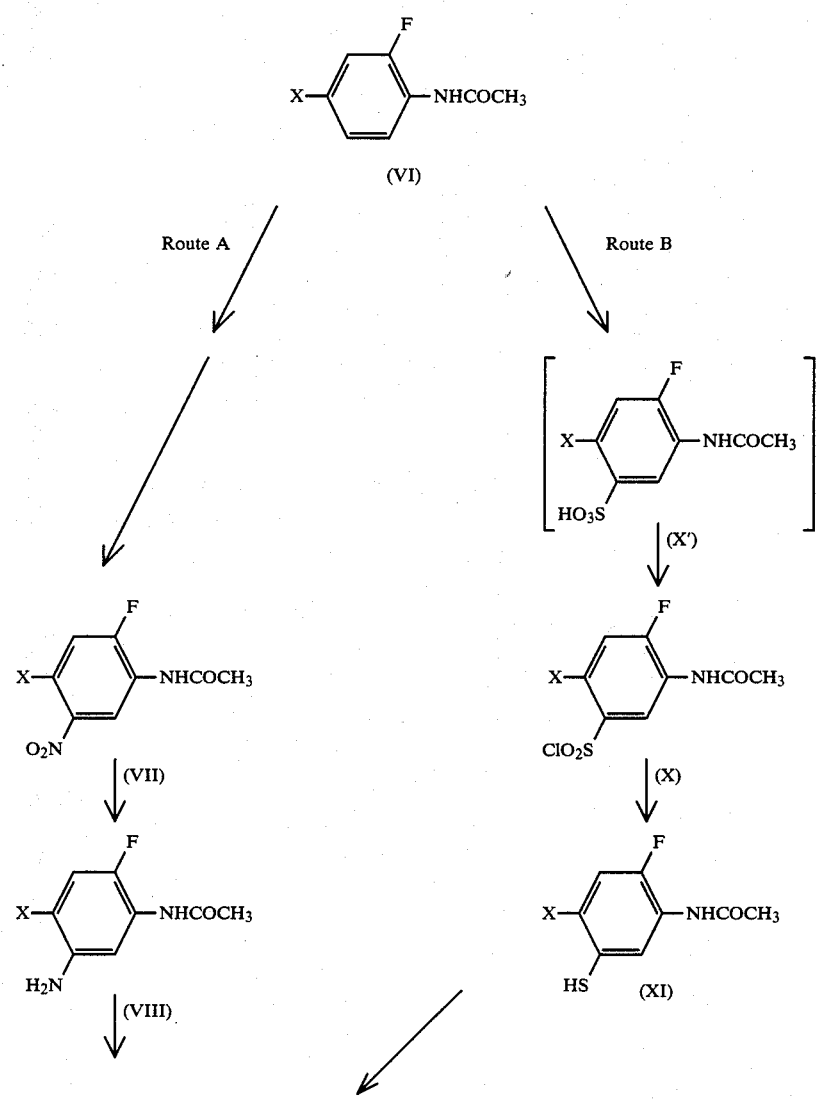

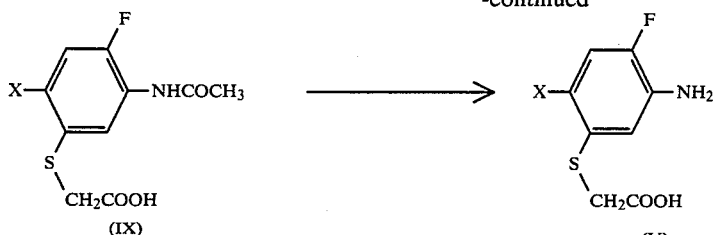

wherein X is as defined above.

The above reactions will be hereinafter explained further in detail:

Route A

The acetanilide (VI) [U.S. Pat. No. 4,001,272] is reacted with a 1.0 to 1.5 equivalent amount of a nitrating agent (e.g. fuming nitric acid, a mixture of fuming nitric acid, sulfuric acid) in a solvent (e.g. fuming sulfuric acid) at a temperature of $-5°$ to $5°$ C. for a period of 0.1 to 6 hours to obtain the acetonitroanilide (VII). The reaction mixture is usually subjected to ordinary post-treatment such as pouring into ice, collecting the resulting precipitates or crystals and washing with water to recover the produced acetonitroanilide (VII). When desired, the product may be purified by a per se conventional procedure such as column chromatography or recrystallization.

Reduction of the acetonitroanilide (VII) may be carried out in a solvent (e.g. water, acetic acid, ethyl acetate, ethanol) in the existence of a 2.5 to 10 equivalent amount of iron and a 1.0 to large excessive amount of acetic acid at a temperature of $50°$ to $100°$ C. for a period of 0.5 to 6 hours to obtain the monoacetylphenylenediamine (VIII). The reaction mixture is usually subjected to ordinary post-treatment such as filtration, extraction of the resultant filtrate with an organic solvent and concentration to recover the produced monoacetylphenylenediamine (VIII). When desired, the product may be purified by per se conventional procedure such as column chromatography or recrystallization.

The monoacetylphenylenediamine (VIII) is reacted with a 1.0 to 1.5 equivalent amount of sodium nitrite in a 1.0 to large excessive amount of a mineral acid (e.g. hydrochloric acid, sulfuric acid) to make a diazonium salt, which is then reacted with a 1.0 to 1.5 equivalent amount of thioglycollic acid in a solvent (e.g. water, acetic acid) in the existence of a 1.0 to 1.2 equivalent amount of a divalent copper salt (e.g. cupric sulfate, basic cupric carbonate) at a temperature of $20°$ to $40°$ C. for a period of 0.2 to 10 hours to obtain the acetylaminophenylthioacetic acid (IX). The reaction mixture is usually subjected to ordinary posttreatment such as filtration, or extraction with an organic solvent and concentration to recover the produced acetylaminophenylthioacetic acid (IX). When desired, the product may be purified by a per se conventional procedure such as column chromatography or recrystallization.

The thus produced acetylaminophenylthioacetic acid (IX) is reacted with a 1.0 to large excessive amount of a mineral acid (e.g. hydrochloric acid, hydrobromic acid, sulfuric acid), if necessary, in a solvent (e.g. water, ethanol, acetic acid), at a temperature of $20°$ to $100°$ C. for a period of 0.5 to 24 hours to obtain the objective aminophenylthioacetic acid (V). The reaction mixture is usually subjected to ordinary post-treatment such as adjusting the pH to 1.5 to 4 with a base (e.g. sodium hydroxide), cooling and collecting the resultant precipitates or crystals, or extraction with an organic solvent and concentration to recover the produced aminophenylthioacetic acid (V). When desired, the product may be purified by a per se conventional procedure such as column chromatography or recrystallization.

Route B

The acetanilide (VI) is reacted with a 1 to 20 equivalent amount of 20 % or higher fuming sulfuric acid, if necessary, in a solvent (e.g. conc. sulfuric acid) at a temperature of $0°$ to $20°$ C. The reaction mixture comprising the produced sulfonic acid is treated with a 1.0 to 10 equivalent amount of a chlorinating agent (e.g. carbon tetrachloride, chloroform, sulfurous dichloride) at a temperature of $60°$ to $65°$ C. for a period of 1 to 96 hours to obtain the sulfonyl chloride (X). The reaction mixture is usually subjected to ordinary post-treatment such as pouring into ice, extraction with an organic solvent and concentration to recover the sulfonyl chloride (X). When desired, the product may be purified by a per se conventional procedure such as recrystallization.

Alternatively, the sulfonyl chloride (X) may be produced by the following procedure. Namely, the acetanilide (VI) is reacted with an equivalent or excessive amount of fuming sulfuric acid in the absence or presence of a solvent (e.g. conc. sulfuric acid) at a temperature of $0°$ to $100°$ C. for a period of 0.5 to 5 hours to produce the sulfonic acid (X'). The reaction mixture is, for instance, dropwise added to ice or ice water, and precipitated crystals are collected by filtration and washed with cooling water. When desired, the thus recovered product may be further purified by recrystallization.

The obtained sulfonic acid (X') is treated with a base such as aqueous sodium hydroxide, aqueous potassium hydroxide or pyridine and concentrated under reduced pressure. The residue is washed with cooling water and collected by filtration to give the corresponding salt (e.g. sodium or potassium salt, pyridine salt).

The above obtained salt of the sulfonic acid (X') is reacted with a 0.1 to 5 equivalent amount of a chlorinating agent such as phosphorus pentachloride or phosphorus oxychloride in the presence or absence of a solvent at a temperature of $0°$ to $200°$ C. for a period of 0.5 to 5 hours to obtain the sulfonyl chloride (X). Examples of the solvent are halogenated hydrocarbons (e.g. chloroform, carbon tetrachloride, dichloroethane, chlorobenzene, dichlorobenzene) and their mixtures. The reaction mixture is usually subjected to ordinary post-treatment such as extraction with an organic solvent and concentration. When desired, the product may be purified by a per se conventional procedure such as column chromatography or recrystallization.

The thus produced sulfonyl chloride (X) is reacted with a 3.0 to 20 equivalent amount of a reducing agent (e.g. zinc, stannous chloride) in the presence of a 3.0 to large excessive amount of an acid (e.g. acetic acid, hydrochloric acid, sulfuric acid) at a temperature of 50° to 100° C. for a period of 0.1 to 24 hours to obtain the thiol (XI). The reaction mixture is usually subjected to ordinary posttreatment such as extraction with an organic solvent and concentration to recover the produced thiol (X). When desired, the product may be purified by a per se conventional procedure such as column chromatography or recrystallization.

The thiol (XI) is reacted with a 1.0 to 1.2 equivalent amount of an α-haloacetic acid (e.g. bromoacetic acid, chloroacetic acid) in an inert solvent such as an aliphatic hydrocarbon (e.g. hexane, heptane), an aromatic hydrocarbon (e.g. benzene, toluene), an ether (e.g. tetrahydrofuran), an amide (e.g. N,N-dimethylformamide), water or dimethylsulfoxide in the presence of a dehydrohalogenating agent such as an organic base (e.g. pyridine, triethylamine) or an inorganic base (e.g. potassium carbonate, sodium carbonate, sodium hydroxide, potassium hydroxide) at a temperature of 0° to 100° C. for a period of 0.5 to 24 hours to obtain the acetaminophenylthioacetic acid (IX). The reaction mixture is usually subjected to ordinary post-treatment such as extraction with an organic solvent and concentration to recover the produced acetaminophenylthioacetic acid (IX). When desired, the product may be purified by a per se conventional procedure such as column chromatography or recrystallization.

Said 5-substituted acetanilides, (VII), (VIII), (IX), (X), (X') and (XI) are representable by the formula:

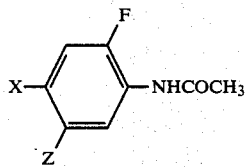

(Z)

wherein Z is —NO$_2$, —NH$_2$, —SCH$_2$COOH, —SO$_2$Cl, —SO$_3$H or —SH. These 5-substituted acetanildies (Z) are novel.

Typical examples of the production of the starting and intermediary compounds are illustratively shown below:

EXAMPLE 2

Production of the N-(carboxymethylthiophenyl)tetrahydrophthalimide (II) from the N-(m-aminophenyl)-tetrahydrophthalimide (IV):

To a mixture of 2-(4-chloro-2-fluoro-5-aminophenyl)-4,5,6,7-tetrahydro-2H-isoindole-1,3-dione (2.9 g), conc. sulfuric acid (5 ml) and water (60 ml), solution of sodium nitrite (0.8 g) in water (4 ml) was dropwise added at −5° to 0° C., and the resultant mixture was stirred at the same temperature for 30 minutes. The reaction mixture was admixed with sulfamic acid to decompose excessive nitrite ion and then dropwise added to a mixture of thioglycollic acid (1.2 g), basic copper carbonate (0.7 g) and water (12 ml) at 25° to 30° C., followed by stirring for 1 hour. The resultant mixture was extracted with ethyl acetate. The extract was washed with water, dried and concentrated to give 2-(4-cloro-2-fluoro-5-carboxymethylthiophenyl)-4,5,6,7-tetrahydro-2H-isoindole-1,3-dione (4.2 g). M.P., 138°–139° C.

EXAMPLE 3

Production of the N-(m-carboxymethylthiophenyl)-tetrahydrophthalimide (II) from the aminophenylthioacetic acid (V):

5-Amino-2-chloro-4-fluorophenylthioacetic acid (55.0 g) and 3,4,5,6-tetrahydrophthalic acid anhydride (38.1 g) were dissolved in acetic acid (250 ml), and the resultant mixture was refluxed for 1 hour under heating. After being allowed to cool, water was added to the mixture, which was then extracted with ethyl acetate. The extract was neutralized with an aqueous solution of sodium hydrogen carbonate, washed with water and dried. The solvent was evaporated by distillation under reduced pressure to give 46.8 g of 2-(4-chloro-2-fluoro-5-carboxymethylthiophenyl)-4,5,6,7-tetrahydro-2H-isoindole-1,3-dione. M.P., 138°–139° C.

In the same manner as above, there was produced 2-(4-bromo-2-fluoro-5-carboxymethylthiophenyl)-4,5,6,7-tetrahydro-2H-isoindole-1,3-dione as a glassy substance.

NMR δ ppm (CDCl$_3$) 1.8 (4H, m), 2.4 (4H, m), 3.65 (2H, s), 7.28 (1H, d), 7.45 (1H, s), 10.2 (1H, m).

IR ν cm$^{-1}$ (neat) 1715.

EXAMPLE 4

Production of the aminophenylthioacetic acid (V) from the acetylaminophenylthioacetic acid (IX):

A suspension of 5-(N-acetylamino)-2-chloro-4-fluorophenylthioacetic acid (89.8 g) in a 10 % aqueous hydrochloric acid solution was refluxed for 2 hours under heating. After being allowed to cool, an aqueous solution of sodium hydroxide was added to make the suspension at pH 4. After ice-cooling, the precipitated crystals were collected by filteration, washed with ice-water and dried to give 55.0 g of 5-amino-2-chloro-4-fluorophenylthioacetic acid.

NMR δ ppm (CDl$_3$+D$_6$-DMSO): 3.55 (2H, s), 6.75 (1H, d), 6.92 (1H, d), 6.2–7.6 (2H, m).

IR ν cm$^{-1}$ (liquid paraffin): 3400, 3300, 1670.

In the same manner as above, there was produced 5-amino-2-bromo-4-fluorophenylthioacetic acid.

NMR δ ppm (CDCl$_3$) 3.6 (2H, s), 6.6 (2H, m), 6.9 (1H, d), 7.1 (1H, d).

IR ν cm$^{-1}$ (liquid paraffin): 3380, 3280, 1670.

EXAMPLE 5

Production of the acetonitroanilide (VII) from the acetanilide (VI):

To 20 % ice-cooled fuming sulfuric acid (50 g), 4-(N-acetylamino)-1-chloro-3-fluorobenzene (9.4 g) was dissolved, followed by gradual addition of fuming nitric acid (3.5 g) while keeping the temperature at 0° to 5° C. The resultant mixture was stirred at the same temperature for 1 hour and poured into ice (50 g). The precipitated crystals were collected by filteration, and the filtrate was washed with water and dried to give 11.6 g of 4-(N-acetylamino)-1-chloro-5-fluoro-2-nitrobenzene. M.P., 124.7°–125.7° C.

In the same manner as above, there was produced 4-(N-acetylamino)-1-bromo-5-fluoro-2-nitrobenzene. M.P., 139.6°–140.6° C.

EXAMPLE 6

Production of the monoacetylphenylenediamine (VIII) from the acetonitroanilide (VII):

Iron powder (31.9 g) were suspended in a 5% acetic acid solution (60 ml), and the suspension was heated to 90° C. A solution of 4-(N-acetylamino)-1-chloro-5-fluoro2-nitrobenzene (13.3 g) in acetic acid (100 ml) and ethyl acetate (70 ml) was dropwise added thereto, and the resultant mixture was refluxed at 80° C. for 2 hours. The reaction mixture was filtered by celite. The filtrate was extracted with ethyl acetate, and the extract was neutralized with a saturated sodium hydrogen carbonate solution. The organic layer was washed with water, dried and concentrated under reduced pressure to give 7.0 g of 4-(N-acetylamino)-2-amino-1-chloro-5-fluorobenzene. M.P., 140.5°–141.5° C.

In the same manner as above, there was produced 4-(N-acetylamino)-2-amino-1-bromo-5-fluorobenzene. M.P., 146.8°–147.8° C.

EXAMPLE 7

Production of the acetylaminophenylthioacetic acid (IX) from the monoacetylphenylenediamine (VIII):

4-(N-Acetylamino)-2-amino-1-chloro-5-fluorobenzene (7.0 g) was suspended in a mixture of conc. hydrochloric acid (9 ml), water (40 ml) and ice (60 g), and the suspension was kept at −5° to 10° C., preferably at 0° to 5° C. A solution of sodium nitrite (2.5 g) in water (8 ml) was dropwise added to the suspension, which was then stirred at the same temperature for 1 hour. To the thus prepared diazonium salt solution, sulfamic acid (0.2 g) was added, and the resultant mixture was added to a mixture of thioglycollic acid (4.1 g), basic cupric carbonate (2.3 g) and water (34 ml) and stirred at 15° to 25° C., followed by stirring for 30 minutes. A 50 % sodium hydroxide solution (8.4 ml) was dropwise added thereto to make pH at 7 to 8, followed by stirring at 95° to 100° C. for 1 hour. The reaction mixture was filtered by celite while hot to remove the copper salt. The filtrate was made acidic with conc. hydrochloric acid (12 ml) and extracted with ethyl acetate. The extract was dried, and the solvent was removed under reduced pressure to give 4.8 g of 5-(N-acetylamino)-2-chloro-4-fluorophenylthioacetic acid. M.P., 145.0°–147.0° C.

In the same manner as above, there was produced 5-(N-acetylamino)-2-bromo-4-florophenylthioacetic acid. M.P., 173.1°–174.1° C.

EXAMPLE 8

Production of the sulfonyl chloride (X) from the acetanilide (VI):

4-Chloro-2-fluoroacetanilide (100 g) was dissolved in conc. sulfuric acid (80 ml) under ice-cooling. 60% fuming sulfuric acid (200 ml) was dropwise added thereto at 0° to 10° C., followed by stirring for 1 hour. Carbon tetrachloride (300 ml) was added to the resultant mixture at room temperature, and the mixture was stirred at 60° to 65° C. for 5 hours. After being allowed to cool to room temperature, carbon tetrachloride (300 ml) was added to the mixture, and the resulting mixture was stirred at 60° to 65° C. for 5 hours. After being allowed to cool, the reaction mixture was poured into ice water, and extracted with ethyl acetate. The extract was washed with water, dried and concentrated to give 139 g of 4-chloro-2-fluoro-5-chlorosulfonylacetanilide. M.P., 138°–139° C.

In the same manner as above, there was produced 4-bromo-2-fluoro-5-chlorosulfonylacetanilide. M.P., 155°–156° C.

EXAMPLE 9

Production of the sulfonyl chloride (X) from the sulfonic acid (X'):

5-(N-Acetylamino)-2-bromo-4-fluorobenzenesulfonic acid (175.8 g) was admixed with pyridine (130 g), and the resulting mixture was stirred for 1 hour. The precipitated crystals were collected by filtration and washed with diethyl ether. The thus obtained pyridinium salt of sulfonic acid (199.5 g) was suspended in chloroform (560 ml), and phosphorus pentachloride (140.7 g) was added thereto. The resultant mixture was stirred at 60 to 70° C. for 1 hour. The reaction mixture was allowed to cool, and water was added thereto, followed by extraction with chloroform. The extract was dried and concentrated to give 73.25 g of 5-(N-acetylamino)-2-bromo-4-fluorobenzenesulfonyl chloride. M.P., 155°–156° C.

In the same manner as above, there was produced 5-(N-acetylamino)-2-chloro-4-fluorobenzenesulfonyl chloride. M.P., 138°–139° C.

EXAMPLE 10

Production of the sulfonic acid (X') from acetanilide (VI):

N-(4-Bromo-2-fluorophenyl)acetamide (173.2 g) was suspended in conc. sulfuric acid (80 ml), and 60% fuming sulfuric acid (340 ml) was dropwise added thereto at 10 to 20° C., followed by stirring at 20° C. for 2 hours. The reaction mixture was dropwise added to ice water (500 g) at 10° to 20° C., and the precipitated crystals were collected by filtration, washed with cold water (400 ml) and dried under reduced pressure to give 175.8 g of 5-(N-acetylamino)-2-bromo-4-fluorobenzenesulfonic acid. M.P., more than 300° C.

NMR δ ppm (D$_6$-DMSO): 2.0 (3H, s), 7.45 (1H, d), 8.3 (1H, d), 9.7 (1H, 3).

In the same manner as above, there was produced 5-(N-acetylamino)-2-chloro-4-fluorobenzenesulfonic acid. M.P., more than 300° C.

NMR δ ppm (D$_6$-DMSO): 2.0 (3H, s), 7.2 (1H, d), 8.2 (1H, d), 9.6 (1H, 3).

EXAMPLE 11

Production of the thiol (XI) from the sulfonyl chloride (X):

4-Bromo-2-fluoro-5-chlorosulfonylacetanilide (73.25 g) was dissolved in acetic acid (630 ml), followed by addition of zinc (289.7 g). The resulting mixture was heated under reflux for 6 hours. After being allowed to cool, water was added thereto. The resultant mixture was extracted with ethyl acetate, washed with water and a sodium dicarbonate solution, dried and concentrated to give 31.38 g of 2-bromo-4-fluoro-5-acetaminothiophenol. M.P., 157°–158° C.

In the same manner as above, there was produced 2-chloro-4-fluoro-5-acetaminothiophenol. M.P., 156°–158° C.

EXAMPLE 12

Production of the acetylaminophenylthioacetic acid (IX) from the thiol (XI):

To a mixture of 2-chloro-4-fluoro-5-acetaminothiophenol (8 g), sodium hydroxide (1.6 g) and water (25 ml), bromoacetic acid (6 g) was dropwise added at 0° to 5° C., and the resultant mixture was refluxed until a lead acetate paper showed a negative value. After being allowed to cool, the reaction mixture was adjusted to pH 4 and extracted with thyl acetate. The extract was dried and concentrated to give 8.8 g of 5-(N-acetylamino)-2-chloro-4-fluorophenylthioacetic acid. M.P., 145°–147° C.

In the same manner as above, there was produced 5-(N-acetylamino)-2-bromo-4-fluorophenylthioacetic acid. M.P., 173.1°–174.1° C.

On the practical usage of the isoindole (I) as a herbicide, it may be applied as such or in any preparation form such as emulsifiable concentrate, wettable powder, suspension, granules, etc. in combination with a conventional solid or liquid carrier or diluent, a surface active agent or an auxiliary agent.

The content of the isoindole (I) as the active ingredient in said preparation form is usually within a range of 0.1 to 90 % by weight, preferably of 0.3 to 80% by weight.

Examples of the solid carrier or diluent are kaolin clay, attapulgite clay, bentonite, terra alba, pyrophyllite, talc, diatomaceous earth, calcite, walnut powders, urea, ammonium sulfate, synthetic hydrated silicon dioxide, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to the one in Table 1.

Formulation Example 1

Fifty parts of Compound No. 2, 3 parts of calcium ligninsulfonate, 2 parts of sodium laurylsulfate and 45 parts of synthetic hydrated silicon dioxide are well mixed while being powdered to obtain a wettable powder.

Formulation Example 2

Ten parts of Compound No. 7, 14 parts of polyoxyethylenestyrylphenyl ether, 6 parts of calcium dodecylbenzenesulfonate, 30 parts of xylene and 40 parts of cyclohexanone are well mixed while being powdered to obtain an emulsifiable concentrate.

Formulation Example 3

Two parts of Compound No. 3, 1 part of synthetic hydrated silicon dioxide, 2 parts of calcium ligninsulfonate, 30 parts of bentonite and 65 parts of kaolin clay are well mixed while being powdered. The mixture is then kneaded with water, granulated and dried to obtain granules.

Formulation Example 4

Twenty-five parts of Compound No. 6 is mixed with 3 parts of polyoxyethylene sorbitan monooleate, 3 parts of CMC (carboxymethyl cellulose) and 69 parts of water and pulverized until the particle size of the active ingredient becomes less than 5 microns to obtain a suspension.

The isoindoles (I) thus formulated in any suitable formulation form are useful for the pre-emergence or post-emergence control of undesired weeds by soil or foliar treatment as well as water treatment. These treatments include the application to the soil surface prior to or after the transplanting or the incorporation into the soil. The foliar treatment may be effected by spraying the herbicidal composition containing the isoindole (I) over the top of plants. It may also be applied directly to weeds with care so as to keep the chemical off the crop foliage.

The isoindoles (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Besides, the isoindoles (I) can be used as herbicides applicable to agricultural plowed field as well as paddy field. They are also useful as herbicides to be employed for orchard, pasture land, lawn, forest, non-agricultural field, etc.

The dosage rate of the isoindoles (I) may vary on prevailing weather conditions, preparation used, prevailing season, mode of application, soil involved, crop and weed species, etc. Generally, however, the dosage rate is from 0.01 to 100 grams, preferably from 0.03 to 50 grams, of the active ingredient per are. In the post-emergence foliar treatment, the dosage rate may be from 0.01 to 10 grams, preferably from 0.03 to 5 grams, of the active ingredient per are. The herbicidal composition of the invention prepared in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface aotive agents as noted above, polyoxyethylene resin acid (ester), ligninsulfonate, abietylenic acid salt, dinaphthylmethanedisulfonate, paraffin, etc. The composition prepared in the form of granules may be normally applied as such without dilution.

The biological data of the isoindoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 2 below were used for comparison.

TABLE 2
| Compound No. | Chemical structure | Remarks |
|---|---|---|
| A | 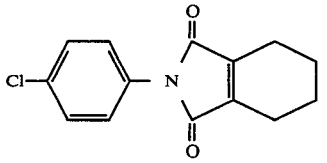 | U.S. Pat. No. 3,878,224 |
| B | 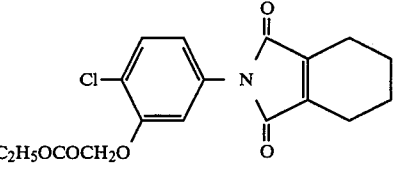 | EP0049508A |
| C | 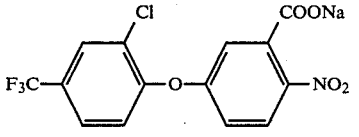 | Commercially available herbicide; "acifluorfen" |
| D | 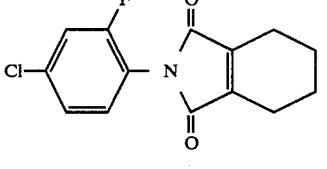 | U.S. Pat. No. 4,032,326 |
| E | 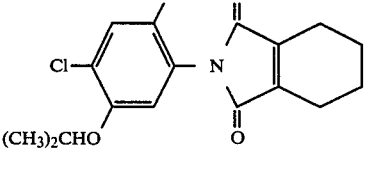 | GB2046754A |
| F | 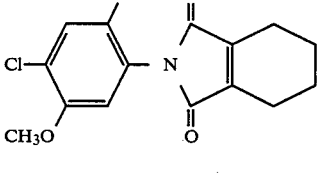 | EP0061741A |
| G | 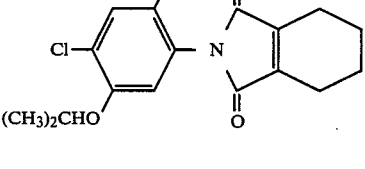 | EP0061741A |
| H | 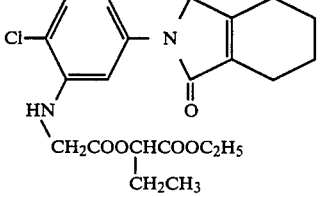 | EP0077938A |

TABLE 2-continued

| Compound No. | Chemical structure | Remarks |
|---|---|---|
| I | 4-chloro-2-fluoro-5-(cyanomethoxy)phenyl tetrahydrophthalimide structure | EP0068822A |
| J | atrazine structure: 2-chloro-4-(isopropylamino)-6-(ethylamino)-1,3,5-triazine | Commercially available herbicide "atrazine" |

TEST EXAMPLE 1

Vats (33 cm×23 cm×11 cm) were filled with upland field soil and the seeds of corn, wheat, soybean, cocklebur, velvetleaf, tall morningglory, hemp sesbania, redroot pigweed, common lambsquarters and black nightshade were sowed therein. Cultivation was carried out in a greenhouse for 18 days. A designed amount of the test compound formulated into an emulsifiable concentrate according to Formulation Example 2 and diluted with water containing a spreading agent was sprayed to the foliage of the test plants over the top by means of a small hand sprayer at a spray volume of 5 liters per are. Thereafter, the test plants were further grown in the greenhouse for 20 days, and the herbicidal activity and the phytotoxicity were examined. At the time of the application, the growing stage of the test plants varied depending on their species but, they were generally at the 1 to 4 leaf stage and 2 to 12 cm in height. The results are shown in Table 3.

TEST EXAMPLE 2

Plastic pots (diameter, 10 cm; height, 10 cm) were filled with upland field soil, and the seeds of tall morningglory and velvetleaf were sowed in the pots, and the soil was covered thereover. A designed amount of the test compound formulated into an emulsifiable concentrate according to Formulation Example 2 and diluted with water was sprayed over the top to the soil surface at a spray volume of 10 liters per are by means of a small hand sprayer, and the soil was well mixed at the depth of 4 cm. Thereafter, the seeds of soybean and cotton were sowed in the pots. The test plants were cultivated in a greenhouse for 20 days and the herbicidal activity was examined. The results are shown in Table 4.

TABLE 4

| Compound No. | Dosage (g/are) | Phytotoxicity Soybean | Phytotoxicity Corn | Herbicidal activity Tall morningglory | Herbicidal activity Velvetleaf |
|---|---|---|---|---|---|
| 1 | 20 | 0 | 0 | 5 | 5 |
|   | 5  | 0 | 0 | 4 | 5 |
| 2 | 20 | 0 | 0 | 5 | 5 |
|   | 5  | 0 | 0 | 4 | 5 |
| 3 | 20 | 0 | 0 | 5 | 5 |

TABLE 3

| Compound No. | Dosage (g/are) | Phytotoxicity Corn | Phytotoxicity Wheat | Phytotoxicity Soybean | Cocklebur | Velvetleaf | Tall morningglory | Hemp sesbania | Redroot pigweed | Common lambsquarters | Black nightshade |
|---|---|---|---|---|---|---|---|---|---|---|---|
| 1 | 0.63 | 2 | 2 | 2 | 5 | 5 | 5 | 5 | 5 | 5 | 5 |
|   | 0.16 | 1 | 0 | 1 | 5 | 5 | 5 | 4 | 5 | 4 | 3 |
| 2 | 0.63 | 2 | 2 | 2 | 5 | 5 | 5 | 5 | 5 | 5 | 5 |
|   | 0.16 | 2 | 1 | 0 | 5 | 5 | 5 | 5 | 4 | 4 | 4 |
| 3 | 0.63 | 2 | 2 | 1 | 5 | 5 | 5 | 5 | 5 | 5 | 5 |
|   | 0.16 | 0 | 0 | 0 | 5 | 5 | 5 | 5 | 5 | 4 | 5 |
| 4 | 0.63 | 2 | 1 | 2 | 5 | 5 | 5 | 5 | 5 | 5 | 5 |
|   | 0.16 | 1 | 1 | 1 | 5 | 5 | 5 | 4 | 4 | 4 | 3 |
| 6 | 0.63 | 2 | 2 | 1 | 5 | 5 | 5 | 5 | 5 | 5 | 5 |
|   | 0.16 | 1 | 1 | 0 | 5 | 5 | 5 | 5 | 5 | 5 | 4 |
| 7 | 0.63 | 2 | 2 | 2 | 5 | 5 | 5 | 5 | 5 | 5 | 5 |
|   | 0.16 | 1 | 0 | 0 | 5 | 5 | 5 | 5 | 5 | 5 | 5 |
| 8 | 0.63 | 1 | 1 | 1 | 5 | 5 | 5 | 5 | 5 | 5 | 5 |
|   | 0.16 | 0 | 0 | 1 | 5 | 5 | 5 | 4 | 5 | 4 | 4 |
| 9 | 0.63 | 1 | 0 | 1 | 5 | 5 | 5 | 5 | 5 | 5 | 5 |
|   | 0.16 | 0 | 0 | 0 | 5 | 5 | 5 | 4 | 5 | 5 | 4 |
| A | 0.63 | 0 | 0 | 1 | 1 | 4 | 2 | 2 | 4 | 3 | 3 |
|   | 0.16 | 0 | 0 | 0 | 0 | 2 | 0 | 1 | 1 | 1 | 0 |
| B | 0.63 | 0 | 0 | 1 | 3 | 5 | 3 | 2 | 4 | 4 | 3 |
|   | 0.16 | 0 | 0 | 0 | 1 | 3 | 1 | 1 | 2 | 2 | 1 |
| C | 2.5  | 0 | 1 | 2 | 4 | 3 | 5 | 5 | 5 | 5 | 4 |
|   | 0.63 | 0 | 0 | 1 | 2 | 1 | 3 | 5 | 4 | 3 | 1 |

TABLE 4-continued

| Compound No. | Dosage (g/are) | Phytotoxicity Soybean | Phytotoxicity Corn | Herbicidal activity Tall morning-glory | Herbicidal activity Velvet-leaf |
|---|---|---|---|---|---|
| 4 | 5 | 0 | 0 | 4 | 5 |
| 4 | 20 | 0 | 0 | 5 | 5 |
| 6 | 5 | 0 | 0 | 5 | 5 |
| 6 | 20 | 0 | 0 | 5 | 5 |
| 7 | 5 | 0 | 0 | 4 | 5 |
| 7 | 20 | 0 | 0 | 5 | 5 |
| 8 | 5 | 0 | 0 | 5 | 5 |
| 8 | 20 | 0 | 0 | 4 | 5 |
| 9 | 5 | 0 | 0 | 5 | 5 |
| 9 | 20 | 0 | 0 | 4 | 5 |

TEST EXAMPLE 3

Cylindrical plastic pots (diameter, 8 cm; height, 12 cm) were filled with paddy field soil, and the seeds of barnyardgrass (*Echinochloa oryzicola*), broad-leaved weeds (e.g. false pimpernel, Indian toothcup, waterwort) and the buds of arrowhead were sowed in 1 to 2 cm depth. Water was poured therein to make a flooded condition. Rice seedlings of the 2-leaf stage were transplanted therein and grown in a greenhouse. Six days thereafter, a designed amount of the test compound formulated in an emulsifiable concentrate according to Formulation Example 2 and diluted with water (5 ml) was applied to the pots by perfusion. The test plants were grown for further 20 days in the greenhouse, and the herbicidal activity and the phytotoxicity were examined. The results are shown in Table 5.

TABLE 5

| Compound No. | Dosage (g/are) | Phytotoxicity Rice plant | Herbicidal activity Barnyard-grass | Herbicidal activity Broad-leaved weed | Herbicidal activity Arrow-head |
|---|---|---|---|---|---|
| 1 | 10 | 1 | 4 | 5 | 5 |
| 2 | 10 | — | 5 | 5 | 5 |
| 3 | 10 | 1 | 4 | 5 | 5 |
| 4 | 10 | — | 4 | 5 | 5 |
| 7 | 10 | 1 | 5 | 5 | 5 |
| 9 | 10 | 0 | 4 | 5 | 5 |

TEST EXAMPLE 4

Cylindrical plastic pots (diameter, 10 cm; height, 10 cm) were filled with upland field soil, and the seeds of barnyardgrass (*Echinochloa crus-galli*), oat (*Avena sativa*), radish and velvetleaf were sowed therein and grown in a greenhouse for 10 days. A designed amount of the test compound formulated in an emulsifiable concentrate according to Formulation Example 2 and diluted with water containing a spreading agent was sprayed to the foliage of the test plants over the top by means of a small hand-sprayer at a spray volume of 10 liters per are. After 20 days' cultivation in the greenhouse, the herbicidal activity was examined. The results are shown in Table 6.

TABLE 6

| Compound No. | Dosage (g/are) | Herbicidal activity Barnyard-grass | Oat | Radish | Velvet-leaf |
|---|---|---|---|---|---|
| 1 | 10 | 5 | 4 | 5 | 5 |
| 2 | 10 | 5 | 3 | 5 | 5 |
| 3 | 10 | 5 | 4 | 5 | 5 |
| 4 | 10 | 5 | 4 | 5 | 5 |
| 6 | 10 | 5 | 3 | 5 | 5 |
| 7 | 10 | 5 | 5 | 5 | 5 |
| 8 | 10 | 4 | 3 | 5 | 5 |
| 9 | 10 | 5 | 4 | 5 | 5 |

TEST EXAMPLE 5

Plural sets of two vats (11 cm×16 cm×7 cm) were filled with upland field soil and the seeds of corn, peanut, soybean, cocklebur, tall morningglory, velvetleaf, black nightshade and prickly sida were sowed therein. Cultivation was carried out in a greenhouse for 18 days. A designed amount of the test compound formulated into an emulsifiable concentrate according to Formulation Example 2 and diluted with water containing a spreading agent was sprayed to the foliage of the test plants over the top by means of a small hand sprayer at a spray volume of 5 liters per are. Thereafter, the test plants were further grown in the greenhouse for 20 days, and the herbicidal activity and the phytotoxicity were examined. At the time of the application, the growing stage of the test plants varied depending on their species but, generally, weeds were at the 2 to 4 leaf stage and 3 to 17 cm in height, while soybean was at the 2 leaf stage and peanut and corn were at the 3 leaf stage. The results are shown in Table 7.

TABLE 7

| Compound No. | Dosage (g/are) | Phytotoxicity Corn | Phytotoxicity Peanut | Phytotoxicity Soybean | Herbicidal activity Cocklebur | Tall morning-glory | Velvet-leaf | Black nightshade | Prickly sida |
|---|---|---|---|---|---|---|---|---|---|
| 1 | 0.08 | 1 | 0 | 0 | 4 | 5 | 5 | 4 | 4 |
| 1 | 0.04 | 0 | 0 | 0 | 3 | 4 | 4 | 3 | 3 |
| 1 | 0.02 | 0 | 0 | 0 | 2 | 2 | 3 | 3 | 2 |
| 2 | 0.08 | 1 | 0 | 0 | 4 | 4 | 5 | 5 | 4 |
| 2 | 0.04 | 0 | 0 | 0 | 4 | 3 | 4 | 4 | 3 |
| 2 | 0.02 | 0 | 0 | 0 | 2 | 2 | 4 | 3 | 1 |
| 3 | 0.08 | 0 | 0 | 0 | 4 | 4 | 5 | 4 | 4 |
| 3 | 0.04 | 0 | 0 | 0 | 4 | 3 | 4 | 3 | 3 |
| 3 | 0.02 | 0 | 0 | 0 | 2 | 2 | 4 | 3 | 2 |
| 4 | 0.08 | 0 | 0 | 0 | 4 | 5 | 5 | 3 | 3 |
| 4 | 0.04 | 0 | 0 | 0 | 3 | 3 | 4 | 3 | 2 |
| 4 | 0.02 | 0 | 0 | 0 | 1 | 2 | 3 | 2 | 1 |
| 5 | 0.08 | 1 | 0 | 0 | 5 | 4 | 5 | 4 | 3 |
| 5 | 0.04 | 0 | 0 | 0 | 3 | 3 | 3 | 3 | 1 |
| 5 | 0.02 | 0 | 0 | 0 | 1 | 1 | 2 | 2 | 1 |
| 6 | 0.08 | 0 | 0 | 0 | 5 | 4 | 4 | 4 | 3 |
| 6 | 0.04 | 0 | 0 | 0 | 3 | 3 | 4 | 3 | 2 |

TABLE 7-continued

| Compound No. | Dosage (g/are) | Phytotoxicity | | | Herbicidal activity | | | | |
|---|---|---|---|---|---|---|---|---|---|
| | | Corn | Peanut | Soybean | Cocklebur | Tall morningglory | Velvetleaf | Black nightshade | Prickly sida |
| | 0.02 | 0 | 0 | 0 | 1 | 2 | 3 | 3 | 1 |
| 7 | 0.08 | 0 | 0 | 0 | 5 | 5 | 5 | 5 | 4 |
| | 0.04 | 0 | 0 | 0 | 4 | 4 | 5 | 4 | 3 |
| | 0.02 | 0 | 0 | 0 | 2 | 3 | 4 | 4 | 2 |
| 8 | 0.08 | 0 | 0 | 0 | 3 | 4 | 4 | 4 | 3 |
| | 0.04 | 0 | 0 | 0 | 2 | 3 | 3 | 3 | 2 |
| | 0.02 | 0 | 0 | 0 | 2 | 1 | 3 | 2 | 1 |
| 10 | 0.08 | 0 | 0 | 0 | 4 | 3 | 4 | 4 | 3 |
| | 0.04 | 0 | 0 | 0 | 3 | 2 | 3 | 3 | 1 |
| | 0.02 | 0 | 0 | 0 | 0 | 1 | 2 | 1 | 1 |
| 11 | 0.08 | 0 | 0 | 0 | 4 | 4 | 5 | 5 | 3 |
| | 0.04 | 0 | 0 | 0 | 3 | 3 | 4 | 4 | 2 |
| | 0.02 | 0 | 0 | 0 | 0 | 2 | 3 | 3 | 1 |
| 12 | 0.08 | 0 | 0 | 0 | 3 | 3 | 4 | 4 | 3 |
| | 0.04 | 0 | 0 | 0 | 2 | 3 | 3 | 3 | 2 |
| | 0.02 | 0 | 0 | 0 | 1 | 1 | 3 | 3 | 1 |
| 14 | 0.08 | 0 | 0 | 0 | 4 | 4 | 5 | 5 | 4 |
| | 0.04 | 0 | 0 | 0 | 3 | 3 | 4 | 4 | 3 |
| | 0.02 | 0 | 0 | 0 | 2 | 1 | 4 | 3 | 1 |
| 15 | 0.08 | 0 | 0 | 0 | 4 | 4 | 5 | 5 | 4 |
| | 0.04 | 0 | 0 | 0 | 4 | 4 | 4 | 4 | 3 |
| | 0.02 | 0 | 0 | 0 | 2 | 2 | 4 | 3 | 1 |
| 16 | 0.08 | 1 | 0 | 0 | 4 | 4 | 5 | 5 | 4 |
| | 0.04 | 0 | 0 | 0 | 3 | 3 | 4 | 4 | 3 |
| | 0.02 | 0 | 0 | 0 | 2 | 2 | 3 | 3 | 1 |
| 17 | 0.08 | 0 | 0 | 0 | 4 | 4 | 5 | 5 | 4 |
| | 0.04 | 0 | 0 | 0 | 2 | 3 | 4 | 4 | 3 |
| | 0.02 | 0 | 0 | 0 | 1 | 2 | 3 | 3 | 1 |
| 18 | 0.08 | 0 | 0 | 0 | 3 | 4 | 5 | 5 | 4 |
| | 0.04 | 0 | 0 | 0 | 3 | 3 | 4 | 4 | 2 |
| | 0.02 | 0 | 0 | 0 | 1 | 2 | 3 | 3 | 1 |
| 19 | 0.08 | 0 | 0 | 0 | 4 | 4 | 5 | 5 | 3 |
| | 0.04 | 0 | 0 | 0 | 2 | 2 | 4 | 4 | 3 |
| | 0.02 | 0 | 0 | 0 | 1 | 2 | 3 | 3 | 2 |
| 20 | 0.08 | 0 | 0 | 0 | 3 | 4 | 5 | 4 | 3 |
| | 0.04 | 0 | 0 | 0 | 1 | 2 | 3 | 4 | 2 |
| | 0.02 | 0 | 0 | 0 | 0 | 0 | 1 | 2 | 1 |
| 21 | 0.08 | 0 | 0 | 0 | 5 | 4 | 5 | 5 | 3 |
| | 0.04 | 0 | 0 | 0 | 4 | 4 | 4 | 4 | 2 |
| | 0.02 | 0 | 0 | 0 | 1 | 2 | 4 | 3 | 1 |
| 22 | 0.08 | 0 | 0 | 0 | 3 | 4 | 5 | 5 | 3 |
| | 0.04 | 0 | 0 | 0 | 2 | 3 | 4 | 4 | 2 |
| | 0.02 | 0 | 0 | 0 | 1 | 1 | 2 | 3 | 2 |
| 23 | 0.08 | 0 | 0 | 0 | 3 | 4 | 4 | 4 | 3 |
| | 0.04 | 0 | 0 | 0 | 3 | 2 | 3 | 3 | 2 |
| | 0.02 | 0 | 0 | 0 | 1 | 1 | 1 | 2 | 1 |
| 24 | 0.08 | 0 | 0 | 0 | 3 | 4 | 4 | 5 | 3 |
| | 0.04 | 0 | 0 | 0 | 2 | 3 | 3 | 4 | 2 |
| | 0.02 | 0 | 0 | 0 | 0 | 2 | 2 | 3 | 2 |
| 25 | 0.08 | 0 | 0 | 0 | 5 | 4 | 5 | 5 | 4 |
| | 0.04 | 0 | 0 | 0 | 4 | 3 | 4 | 4 | 3 |
| | 0.02 | 0 | 0 | 0 | 2 | 2 | 3 | 3 | 1 |
| 26 | 0.08 | 0 | 0 | 0 | 3 | 4 | 5 | 5 | 3 |
| | 0.04 | 0 | 0 | 0 | 2 | 3 | 4 | 4 | 2 |
| | 0.02 | 0 | 0 | 0 | 1 | 1 | 3 | 3 | 1 |
| 27 | 0.08 | 0 | 0 | 0 | 4 | 4 | 4 | 4 | 3 |
| | 0.04 | 0 | 0 | 0 | 3 | 3 | 4 | 4 | 2 |
| | 0.02 | 0 | 0 | 0 | 0 | 2 | 2 | 3 | 1 |
| 28 | 0.08 | 0 | 0 | 0 | 3 | 4 | 5 | 4 | 3 |
| | 0.04 | 0 | 0 | 0 | 2 | 3 | 4 | 3 | 2 |
| | 0.02 | 0 | 0 | 0 | 1 | 1 | 2 | 3 | 1 |
| A | 0.08 | 0 | 0 | 0 | 0 | 0 | 1 | 0 | 0 |
| | 0.04 | 0 | 0 | 0 | 0 | 0 | 0 | 0 | 0 |
| | 0.02 | 0 | 0 | 0 | 0 | 0 | 0 | 0 | 0 |
| B | 0.08 | 0 | 0 | 0 | 1 | 1 | 1 | 2 | 0 |
| | 0.04 | 0 | 0 | 0 | 0 | 0 | 0 | 1 | 0 |
| | 0.02 | 0 | 0 | 0 | 0 | 0 | 0 | 0 | 0 |
| D | 0.08 | 1 | 2 | 2 | 0 | 2 | 3 | 5 | 3 |
| | 0.04 | 1 | 1 | 2 | 0 | 2 | 1 | 4 | 1 |
| | 0.02 | 0 | 1 | 1 | 0 | 1 | 0 | 3 | 0 |
| E | 0.08 | 1 | 0 | 1 | 0 | 0 | 1 | 4 | 0 |
| | 0.04 | 0 | 0 | 0 | 0 | 0 | 0 | 3 | 0 |
| | 0.02 | 0 | 0 | 0 | 0 | 0 | 0 | 2 | 0 |
| F | 0.08 | 2 | 3 | 4 | 3 | 4 | 5 | 5 | 3 |
| | 0.04 | 1 | 2 | 3 | 2 | 4 | 3 | 5 | 2 |
| | 0.02 | 1 | 2 | 3 | 1 | 2 | 2 | 4 | 1 |
| H | 0.08 | 1 | 0 | 0 | 2 | 3 | 3 | 3 | 3 |

TABLE 7-continued

| Com-pound No. | Dosage (g/are) | Phytotoxicity | | | Herbicidal activity | | | | |
|---|---|---|---|---|---|---|---|---|---|
| | | Corn | Peanut | Soy-bean | Cock-lebur | Tall morning-glory | Velvet-leaf | Black night-shade | Prickly sida |
| | 0.04 | 1 | 0 | 0 | 0 | 1 | 2 | 3 | 2 |
| | 0.02 | 0 | 0 | 0 | 0 | 0 | 2 | 1 | 0 |
| I | 0.08 | 3 | 3 | 3 | 4 | 5 | 4 | 5 | 5 |
| | 0.04 | 1 | 2 | 3 | 3 | 4 | 3 | 5 | 4 |
| | 0.02 | 1 | 0 | 1 | 1 | 3 | 2 | 4 | 3 |

TEST EXAMPLE 6

Seeds of soybean, velvetleaf, prickly sida, redroot pigweed, black nightshade, field bindweed and hemp sesbania were sowed in the field as previously laid up in ridges and divided into plots of 3 m², each ridge having a upper width of 1 m. When soybean grew to the 1.5 leaf stage, a designed amount of the test compound formulated into an emulsifiable concentrate according to Formulation Example 2 was dispersed in water containing a spreading agent and sprayed to the foliage of the test plants by means of a small hand sprayer at a spray volume of 3.5 liters per are. The application was made with three replications. At the time of the application, the test plants were generally in 2 to 5 leaf stages, while the leaf stages varied depending on the species. After cultivation for 7 days, the herbicidal activity on the weeds as well as the phytotoxicity on soybean were evaluated as follows: the aerial parts of the test plants were cut off and weighed (fresh weight); the percentage of the fresh weight of the treated plant to that of the untreated plant was calculated; and the crop damage and the herbicidal activity were evaluated by the standard given in Table 8.

TABLE 8

| Rating value | Fresh weight (percentage to untreated plot) (%) | |
|---|---|---|
| | Weeds | Soybean |
| 0 | 91– | 91– |
| 1 | 71–90 | 71–90 |
| 2 | 41–70 | 51–70 |
| 3 | 11–40 | 31–50 |
| 4 | 4–10 | 11–30 |
| 5 | 0–3 | 0–10 |

The results are shown in Table 9.

TABLE 9

| Compound No. | Dosage (g/are) | Phyto-toxicity Soybean | Velvet-leaf | Prickly sida | Redroot pigweed | Black night-shade | Field bind-weed | Hemp sesbania |
|---|---|---|---|---|---|---|---|---|
| 7 | 0.5 | 1 | 5 | 5 | 5 | 5 | 5 | 5 |
| | 0.25 | 0 | 5 | 4 | 5 | 5 | 4 | 4 |
| | 0.125 | 0 | 5 | 3 | 4 | 4 | 4 | 2 |
| C | 3 | 1 | 3 | 2 | 4 | 4 | 4 | 5 |
| | 1.5 | 0 | 1 | 1 | — | — | 3 | — |

TEST EXAMPLE 7

(a) Seeds of cocklebur, annual morningglory, velvetleaf, redroot pigweed and jimsonweed were sowed in the field as previously laid up in ridges and divided into plots of 3 m², each ridge having a upper width of 1 m. When the weeds grew to 2 to 5 leaf stage, a designed amount of the test compound formulated into an emulsifiable concentrate according to Formulation Example 2 was diluted with water containing a spreading agent and sprayed to the foliage of the test plants by means of a small hand sprayer at a spray volume of 5 liters per are. The application was made with three replications. After cultivation for 26 days, the herbicidal activity on the weeds were evaluated as follows: the aerial parts of the test plants were cut off and weighed (fresh weight); the percentage of the fresh weight of the treated plant to that of the untreated plant was calculated; and the herbicidal activity was evaluated by the standard given in Table 10(a).

TABLE 10(a)

| Rating value | Fresh weight (percentage to untreated plot) (%) |
|---|---|
| 0 | 91– |
| 1 | 71–90 |
| 2 | 41–70 |
| 3 | 11–40 |
| 4 | 4–10 |
| 5 | 0–3 |

The results are shown in Table 11(a).

TABLE 11(a)

| Com-pound No. | Dos-age (g/are) | Herbicidal activity | | | | |
|---|---|---|---|---|---|---|
| | | Cock-lebur | Annual morning-glory | Velvet-leaf | Redroot pigweed | Jimson-weed |
| 7 | 1 | 5 | 5 | 5 | 5 | 5 |
| | 0.5 | 5 | 5 | 5 | 5 | 5 |
| | 0.25 | 4 | 3 | 5 | 5 | — |
| G | 1 | 5 | 5 | 5 | 5 | 5 |
| | 0.5 | 5 | 5 | 5 | 5 | 5 |
| | 0.25 | 4 | 3 | 5 | — | 5 |
| J | 20 | 4 | 5 | 4 | 5 | 5 |
| | 10 | 3 | 4 | 3 | — | — |

(b) Seeds of corn were sowed in the field as previously laid up in ridges and divided into plots of 3 m², each ridge having a upper width of 1 m. When they grew to 4 leaf stage, a designed amount of the test compound formulated into an emulsifiable concentrate according to Formulation Example 2 was diluted with water containing a spreading agent and sprayed to the foliage of the test plants by means of a small hand sprayer at a spray volume of 5 liters per are. The application was made with three replications. After cultivation for each 6 and 40 days, the phytotoxicity was evaluated as follows: the aerial parts of the test plants were cut off and weighed (fresh weight); the percentage of the fresh weight of the treated plant to that of the untreated plant was calculated; and the crop damage was evaluated by the standard given in Table 10(b).

TABLE 10(b)

| Rating value | Fresh weight (percentage to untreated plot) (%) |
| --- | --- |
| 0 | 91– |
| 1 | 71–90 |
| 2 | 41–70 |
| 3 | 11–40 |
| 4 | 4–10 |
| 5 | 0–3 |

The results are shown in table 11(b).

TABLE 11(b)

| Compound No. | Dosage (g/are) | Phytotoxicity to corn | |
| --- | --- | --- | --- |
| | | 6 Days | 40 Days |
| 7 | 1 | 2 | 1 |
| | 0.5 | 1 | 0 |
| | 0.25 | 1 | 0 |
| G | 1 | 3 | 1 |
| | 0.5 | 3 | 1 |

TABLE 11(b)-continued

| Compound No. | Dosage (g/are) | Phytotoxicity to corn | |
| --- | --- | --- | --- |
| | | 6 Days | 40 Days |
| | 0.25 | 2 | 0 |
| J | 20 | 0 | 0 |
| | 10 | 0 | 0 |

What is claimed is:

1. A 2-(2-fluoro-4-halo-5-carboxymethylthiophenyl)4,5,6,7-tetrahydro-2H-isoindole-1,3-dione of the formula:

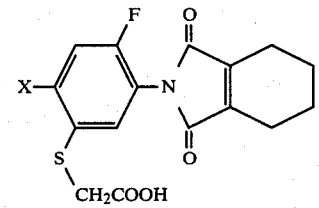

wherein X is a chlorine atom or a bromine atom.

2. A compound according to claim 1, wherein X is a chlorine atom.

3. A compound according to claim 1, wherein x is a bromine atom.

* * * * *